(12) United States Patent
Jeon et al.

(10) Patent No.: US 8,808,927 B2
(45) Date of Patent: Aug. 19, 2014

(54) NONAQUEOUS ELECTROLYTE LITHIUM SECONDARY BATTERY

(75) Inventors: Jong-Ho Jeon, Daejeon (KR); Soo-Jin Kim, Daejeon (KR); Ho-Chun Lee, Daejeon (KR)

(73) Assignee: LG Chem, Ltd. (KR)

( * ) Notice: Subject to any disclaimer, the term of this patent is extended or adjusted under 35 U.S.C. 154(b) by 497 days.

(21) Appl. No.: 12/740,491

(22) Filed: Apr. 29, 2010

(65) Prior Publication Data

US 2012/0202123 A1    Aug. 9, 2012

Related U.S. Application Data

(63) Continuation of application No. PCT/KR2009/006557, filed on Nov. 9, 2009.

(30) Foreign Application Priority Data

Nov. 11, 2008  (KR) .................. 10-2008-0111562

(51) Int. Cl.

| | |
|---|---|
| *H01M 6/16* | (2006.01) |
| *H01M 6/04* | (2006.01) |
| *C01G 53/00* | (2006.01) |
| *H01M 10/0525* | (2010.01) |
| *H01M 4/36* | (2006.01) |
| *H01M 10/0567* | (2010.01) |
| *C07D 317/14* | (2006.01) |
| *C07D 317/36* | (2006.01) |
| *C01G 51/00* | (2006.01) |
| *H01M 4/525* | (2010.01) |
| *C01G 45/12* | (2006.01) |
| *H01M 10/0569* | (2010.01) |
| *H01M 10/42* | (2006.01) |

(52) U.S. Cl.
CPC .............. *C07D 317/14* (2013.01); *C01G 53/52* (2013.01); *H01M 2300/0042* (2013.01); *C01P 2006/40* (2013.01); *H01M 10/0525* (2013.01); *C01G 53/50* (2013.01); *H01M 4/364* (2013.01); *H01M 10/0567* (2013.01); *C07D 317/36* (2013.01); *Y02E 60/122* (2013.01); *C01G 51/50* (2013.01); *H01M 4/525* (2013.01); *H01M 2300/0037* (2013.01); *C01G 45/1228* (2013.01); *H01M 10/0569* (2013.01); *H01M 10/4235* (2013.01); *H01M 2300/004* (2013.01); *C01G 51/42* (2013.01)

USPC .......................... 429/331; 429/332; 429/188

(58) Field of Classification Search
CPC .................... H01M 6/04; H01M 6/16
USPC .......................... 429/331, 332, 188
See application file for complete search history.

(56) References Cited

U.S. PATENT DOCUMENTS

| | | |
|---|---|---|
| 2004/0013946 A1 | 1/2004 | Abe et al. |
| 2005/0014069 A1 | 1/2005 | Fukushima et al. |
| 2005/0084765 A1 | 4/2005 | Lee et al. |
| 2006/0216601 A1 | 9/2006 | Komiyama et al. |
| 2007/0026315 A1* | 2/2007 | Lampe-Onnerud et al. .. 429/224 |
| 2008/0220336 A1 | 9/2008 | Mun et al. |

FOREIGN PATENT DOCUMENTS

| | | | | |
|---|---|---|---|---|
| CN | 1832231 A | 9/2006 | | |
| JP | 2004265832 A | 9/2004 | | |
| JP | 2005072003 A | 3/2005 | | |
| JP | 2007220313 A | 8/2007 | | |
| JP | 2008235008 A | * 10/2008 | ............ | H01M 10/36 |
| KR | 20020026654 A | 4/2002 | | |
| KR | 10-2006-0016678 A | 2/2006 | | |
| KR | 10-0571267 B1 | 4/2006 | | |
| KR | 10-2008-0054100 A | 6/2008 | | |
| KR | 10-2008-0082276 A | 9/2008 | | |
| TW | 200539493 | 12/2005 | | |

OTHER PUBLICATIONS

English Translation of JP 2008235008.*
ISR of PCT/KR2009/006557 dated Jul. 7, 2010.

* cited by examiner

*Primary Examiner* — Patrick Ryan
*Assistant Examiner* — Kiran Quraishi
(74) *Attorney, Agent, or Firm* — Lerner, David, Littenberg, Krumholz & Mentlik, LLP

(57) ABSTRACT

A lithium secondary battery comprises an anode capable of intercalating or disintercalating lithium ions, a cathode configured with a lithium-containing oxide, and a nonaqueous electrolyte solution. The lithium-containing oxide comprises a lithium nickel based oxide. The nonaqueous electrolyte solution comprises vinyl ethylene carbonate (VEC) and a mono-nitrile compound. This lithium secondary battery solves the deterioration of charge/discharge cycle characteristics caused by a lithium nickel based oxide used for a cathode, and also controls the decomposition reaction of electrolyte to solve the swelling phenomenon even though the battery is stored at a high temperature or charged/discharged in a fully-charged state, thereby improving high-temperature life characteristics.

18 Claims, No Drawings

NONAQUEOUS ELECTROLYTE LITHIUM SECONDARY BATTERY

CROSS-REFERENCE TO RELATED APPLICATIONS

The present application is a continuation of International Application No. PCT/KR2009/006557, filed on Nov. 9, 2009, which claims priority under 35 U.S.C. 119 to Korean Patent Application No. 10-2008-0111562 filed in Republic of Korea on Nov. 11, 2008, the disclosure of which is hereby incorporated herein by reference.

TECHNICAL FIELD

The present invention relates to a nonaqueous electrolyte lithium secondary battery, and particularly to a nonaqueous electrolyte lithium secondary battery comprising a lithium nickel based oxide.

BACKGROUND OF THE INVENTION

Along with the technical development on mobile instruments as well as the increased demands thereon, more secondary batteries are needed as an energy source. Among such secondary batteries, lithium secondary batteries are widely used due to high energy density and voltage, long life cycle and low self-discharge rate.

Lithium-containing cobalt oxide ($LiCoO_2$) is frequently used for a cathode of a lithium secondary battery as a cathode active material. Aside from it, lithium-containing manganese oxides such as $LiMnO_2$ with a layered crystalline structure and $LiMn_2O_4$ with a spinel crystalline structure and lithium nickel based oxides such as $LiNiO_2$ comprising lithium and nickel together are also considered.

Among the above cathode active materials, $LiCoO_2$ is currently widely used due to its excellent properties, for example excellent cycle characteristics. However, $LiCoO_2$ has bad safety and is very expensive since its raw material, cobalt, is very rare. In addition, $LiCoO_2$ is not suitable for mass production, which is a prerequisite as a power source for electric vehicles or the like.

Lithium manganese oxides such as $LiMnO_2$ and $LiMn_2O_4$ are advantageous in that their raw material, manganese, is abundant and nature-friendly. In this reason, lithium manganese oxides attract much interest as a cathode active material substituting for $LiCoO_2$. However, such lithium manganese oxides have small capacity and bad cycle characteristics.

Meanwhile, lithium nickel based oxides such as $LiNiO_2$ are cheaper than the cobalt based oxides and nevertheless exhibit high discharge capacity when being charged to 4.3V. In addition, a doped $LiNiO_2$ has a reversible capacity approaching about 200 mAh/g, which exceeds a capacity of $LiCoO_2$ (about 165 mAh/g). Thus, a battery using the lithium nickel based oxide as a cathode has an improved energy density, so the lithium nickel based oxide is actively studied to develop high-capacity batteries.

However, secondary batteries adopting lithium nickel based oxides are not easily put into practice due to the following reasons.

First, charge/discharge cycle characteristics are not good.

Second, nickel has greater reactivity than cobalt and manganese. Thus, when a battery is stored at a high temperature or charged/discharged in a fully-charged state, the swelling phenomenon caused by a decomposition reaction of nonaqueous electrolyte becomes more serious. As a result, particularly in case of angled batteries and pouch batteries, the thickness of battery is increased, and it is very disadvantageous in a set such as cellular phones and notebooks. In other words, when being left alone at a high temperature, such batteries are not safe.

SUMMARY OF THE INVENTION

The present invention is designed to solve the problems of the prior art, and therefore an aspect of the present invention is to provide a lithium secondary battery in which the deterioration of charge/discharge cycle characteristics caused by a lithium nickel based oxide used for a cathode is solved, and also the decomposition reaction of electrolyte is controlled to solve the swelling phenomenon even though the battery is stored at a high temperature or charged/discharged in a fully-charged state.

Another aspect of the present invention is to provide a lithium secondary battery, which comprises an anode capable of intercalating or disintercalating lithium ions, a cathode configured with a lithium-containing oxide, and a nonaqueous electrolyte solution, wherein the lithium-containing oxide comprises a lithium nickel based oxide, and wherein the nonaqueous electrolyte solution comprises vinyl ethylene carbonate (VEC) of the following chemistry figure 1 and a mono-nitrile compound of the following chemistry figure 2 at the same time,

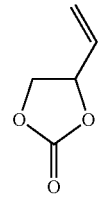

<Chemistry Figure 1>

<Chemistry Figure 2> where R11 is an alkyl group having 2 to 6 carbons.

The lithium nickel based oxide may be any one selected from the group consisting of $LiNiO_2$, $Li_{1-x}(Ni_aCo_bMn_c)O_2$ ($-0.1 \leq x \leq 0.1$, $0<a<1$, $0<b<1$, $0<c<1$, $a+b+c=1$), $LiNiCo_{1-y}O_2$ ($0 \leq y \leq 1$), $LiNi_{1-y}Mn_yO_2$ ($0 \leq y < 1$), $Li(Ni_aCo_bMN_c)O_4$ ($0<a<2$, $0<b<2$, $0<c<2$, $a+b+c=2$) and $LiMn_{2-z}Ni_zO_4$ ($0<z<2$), or their mixtures.

The mono-nitrile compound may be any one selected from the group consisting of propionitrile, butyronitrile, valeronitrile, hexanitrile and heptanenitrile, and their mixtures.

The amount of the vinyl ethylene carbonate is preferably 0.1 to 5.0 parts by weight based on 100 parts by weight of the nonaqueous electrolyte solution, and the amount of the mononitrile compound is preferably 0.1 to 10.0 parts by weight based on 100 parts by weight of the nonaqueous electrolyte solution.

In the lithium secondary battery according to the present invention, the nonaqueous electrolyte solution preferably comprises a mixed organic solvent including a cyclic carbonate compound of the following chemistry figure 3 and a linear carbonate compound of the following chemistry figure 4, and further including a linear ester compound of the following chemistry figure 5,

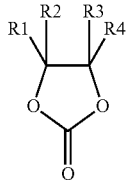

<Chemistry Figure 3> where R1 to R4 are any one selected from the group consisting of hydrogen atoms, fluorine and alkyl groups having 1 to 4 carbons, independently,

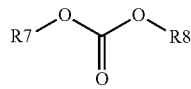

<Chemistry Figure 4> where R7 and R8 are alkyl groups having 1 to 4 carbons, independently, wherein at least one hydrogen atom of the alkyl group is replaceable with fluorine,

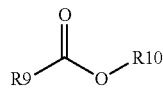

<Chemistry Figure 5> where R9 and R10 are alkyl groups having 1 to 4 carbons, independently, wherein at least one hydrogen atom of the alkyl group is replaceable with fluorine.

Also, in the lithium secondary battery according to the present invention, the nonaqueous electrolyte solution may comprise a mixed organic solvent comprising a cyclic carbonate compound of the following chemistry figure 3 and a linear ester compound of the following chemistry figure 5.

The lithium secondary battery according to the present invention may solve the deterioration of charge/discharge cycle characteristics caused by a lithium nickel based oxide used for a cathode, and also controls the decomposition reaction of electrolyte to solve the swelling phenomenon even though the battery is stored at a high temperature or charged/discharged in a fully-charged state, thereby improving high-temperature life characteristics of the battery.

DETAILED DESCRIPTION

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation.

A lithium secondary battery according to the present invention comprises an anode capable of intercalating or disintercalating lithium ions, a cathode configured with a lithium-containing oxide, and a nonaqueous electrolyte solution. The lithium-containing oxide comprises a lithium nickel based oxide. Also, the nonaqueous electrolyte solution comprises vinyl ethylene carbonate (VEC) of the following chemistry figure 1 and a mono-nitrile compound of the following chemistry figure 2 at the same time,

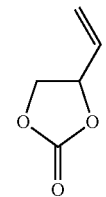

<Chemistry Figure 1>

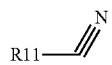

<Chemistry Figure 2> where R11 is an alkyl group having 2 to 6 carbons.

As mentioned above, the battery using a lithium nickel based oxide as a cathode may be manufactured as a high-capacity battery, but the deterioration of charge/discharge cycle characteristics and the swelling phenomenon of battery should be solved in advance. The inventors found that, if a nonaqueous electrolyte solution containing vinyl ethylene carbonate (VEC) and mono-nitrile at the same time is applied to a lithium secondary battery using a lithium nickel based oxide as a cathode, the deterioration of charge/discharge cycle characteristics is solved. Also, the inventors found that, though the battery is stored at a high temperature or charged/discharged in a fully-charged state, the decomposition reaction of the electrolyte is controlled, so the swelling phenomenon is solved. In this standpoint, the inventors have completed this invention.

The lithium nickel based oxide may employ $LiNiO_2$, $Li_{1-x}(Ni_aCo_bMn_c)O_2$ (wherein $-0.1 \leq x \leq 0.1$, $0 < a < 1$, $0 < b < 1$, $0 < c < 1$, and $a+b+c=1$), $LiNi_{1-y}Co_yO_2$ (wherein $0 \leq y < 1$), $LiNi_{1-y}Mn_yO_2$ (wherein $0 \leq y \leq 1$), $Li(Ni_aCo_bMn_c)O_4$ (wherein $0 < a < 2$, $0 < b < 2$, $0 < c < 2$, and $a+b+c=2$) and $LiMn_{2-z}Ni_3O_4$ (wherein $0 < z < 2$), in single or in mixture. More preferably, the lithium nickel based oxide may employ $Li_{1-x}(Ni_aCo_bMn_c)O_2$ (wherein $-0.1 \leq x \leq 0.1$, $0 < a < 1$, $0 < b < 1$, $0 < c < 1$, and $a+b+c=1$), most preferably $Li_{1-x}(Ni_aCo_bMn_c)O_2$ (wherein $-0.1 \leq x \leq 0.1$, $0.5 \leq a \leq 0.8$, $0.1 \leq b \leq 0.2$, $0.1 \leq c \leq 0.3$, and $a+b+c=1$).

Also, the lithium-containing oxide used as a cathode may use the lithium nickel based oxide and $LiCoO_2$ in mixture to improve the cycle characteristics.

In addition, the mono-nitrile compound of the chemistry figure 2 may use propionitrile, butyronitrile, valeronitrile, hexanitrile and heptanenitrile, in single or in mixture, more preferably butyronitrile and valeronitrile, in single or in mixture.

In the lithium secondary battery of the present invention, the amount of the vinyl ethylene carbonate is preferably about 0.1 to about 5.0 parts by weight based on 100 parts by weight of the nonaqueous electrolyte solution, and the amount of the mono-nitrile compound is preferably about 0.1 to about 10.0 parts by weight based on 100 parts by weight of the nonaqueous electrolyte solution. If the amount of the vinyl ethylene carbonate is less than about 0.1 parts by weight, it is difficult to form sufficient SEI (Solid-Electrolyte Interface) on an electrode, thereby deteriorating the effects of the present invention. If the amount of the vinyl ethylene carbonate exceeds about 5.0 parts by weight, the resistance of SEI formed on an electrode may be increased to deteriorate the performance of the battery. Also, if the amount of the mononitrile compound is less than about 0.1 parts by weight, the swelling phenomenon of a battery may not be sufficiently controlled at a high temperature. If the amount of the mononitrile compound exceeds about 10 parts by weight, the performance of battery such as life cycle may be deteriorated.

In the lithium secondary battery of the present invention, the nonaqueous electrolyte solution may employ an organic electrolyte solution commonly used in the art, for example a cyclic carbonate compound of the following chemistry figure 3 and a linear carbonate compound of the following chemistry figure 4, or their mixtures. The nonaqueous electrolyte solution preferably comprises a mixed organic solvent composed of a cyclic carbonate compound and a linear carbonate compound, and more preferably further contains a linear ester compound of the following chemistry figure 5, <Chemistry Figure 3>

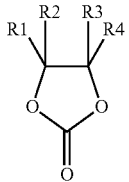

where R1 to R4 are any one selected from the group consisting of hydrogen atoms, fluorine and alkyl groups having 1 to 4 carbons, independently, <Chemistry Figure 4>

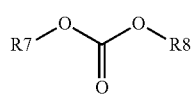

where R7 and R8 are alkyl groups having 1 to 4 carbons, independently, wherein at least one hydrogen atom of the alkyl group is replaceable with fluorine, <Chemistry Figure 5>

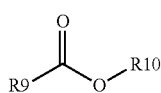

where R9 and R10 are alkyl groups having 1 to 4 carbons, independently, wherein at least one hydrogen atom of the alkyl group is replaceable with fluorine.

In addition, the nonaqueous electrolyte solution preferably comprises a mixed organic solvent comprising the cyclic carbonate compound of the chemistry figure 3 and the linear ester compound of the chemistry figure 5.

The cyclic carbonate compound easily dissociates lithium salts in an electrolyte, so it contributes to the improvement of charging/discharging capacity of a battery. The cyclic carbonate compound of the chemistry figure 3 may employ ethylene carbonate, propylene carbonate, fluoroethylene carbonate and butylene carbonate, in single or in mixture. In particular, ethylene carbonate, or a mixture of ethylene carbonate and propylene carbonate, has a high dielectric constant, so it may more easily dissociate lithium salts in an electrolyte. In case the mixture of ethylene carbonate and propylene carbonate is used, a volume ratio of propylene carbonate is preferably about ¼ to about 1 with respect to ethylene carbonate.

In addition, the linear carbonate compound of the chemistry figure 4 may contribute to the improvement of charging/discharging efficiency of a lithium secondary battery and the optimization of battery characteristics, and such a compound may be dimethyl carbonate, diethyl carbonate, ethylmethyl carbonate or methylpropyl carbonate, which may be used as a mixture.

Meanwhile, the linear ester compound of the chemistry figure 5 is a low-viscosity low-melting point organic solvent having a low freezing point and a relatively high boiling point and exhibiting excellent low-temperature characteristics. Also, the linear ester compound shows relatively low reactivity in comparison to a carbon anode. Such a linear ester compound may contribute to the improvement of low-temperature discharge characteristics and life characteristics of a lithium secondary battery when being mixed with the above cyclic carbonate compound. In other words, the linear ester compound exhibits high ion conductivity at a normal or low temperature by suitably coordinating lithium ions, thereby improving low-temperature discharge characteristic and high-rate discharge characteristics of a battery. Also, an oxidation voltage, which is an inherent characteristic of a solvent, is 4.5V or above, so the linear ester compound gives a resistance against the electrolyte decomposition reaction at a cathode during a charging process, thereby improving the life characteristic of a battery. In addition, wettability to an electrode is improved in comparison to the case that only an ester carbonate based solvent is used as a nonaqueous electrolyte solution, so the formation of lithium dendrite on an electrode surface is controlled, thereby contributing to the improvement of safety of a battery. Such a linear ester compound of the chemistry figure 5 may be methyl acetate, ethyl acetate, propyl acetate, methyl propionate, ethyl propionate or propyl propionate. More preferably, the linear ester compound may use ethyl propionate, ethyl 3-fluoropropanoate, ethyl 3,3-difluoropropanoate, ethyl 3,3,3-trifluoropropanoate, 2-fluoroethyl propionate, 2,2-difluoroethyl propionate, 2,2,2-trifluoroethyl propionate, 2,2,2-trifluoroethyl 3-fluoropropanoate, 2,2,2-trifluoroethyl 3,3-difluoropropanoate and 2,2,2-trifluoroethyl 3,3,3-trifluoropropanoate, independently or mixtures thereof.

In addition, the lithium salt included in the nonaqueous electrolyte solution as an electrolyte may use any salt commonly used in nonaqueous electrolyte solutions for lithium secondary batteries. Representatively, the lithium salt may be $LiPF_6$, $LiBF_4$, $LiSbF_6$, $LiAsF_6$, $LiClO_4$, $LiN(C_2F_5SO_2)_2$, $LiN(CF_3SO_2)_2$, $CF_3SO_3Li$, $LiC(CF_3SO_2)_3$ and so on. Besides, other compounds such as vinyl ethylene carbonate, succinonitrile, cyclohexyl benzene, biphenyl and 1,3-dioxolan-2-onylmethyl allyl sulfonate may be further comprised in the non-aqueous electrolyte solution of the lithium secondary battery to improve cell safety without deteriorating the purpose of the present invention.

The anode capable of intercalating or disintercalating lithium ions used in the lithium secondary battery according to the present invention may employ any material commonly used in making a lithium secondary battery. For example, as carbon materials frequently used as an anode capable of intercalating or disintercalating lithium ions, both low-crystalline carbon and high-crystalline carbon may be used. The low-crystalline carbon is representatively soft carbon or hard carbon, and the high-crystalline carbon is representatively natural graphite, Kish graphite, pyrolytic carbon, mesophase pitch based carbon fiber, meso-carbon microbeads, mesophase pitches, and high-temperature sintered carbon such as petroleum or coal tar pitch derived cokes. At this time, the anode may comprise a binding agent, which may employ various kinds of binder polymer such as vinylidenefluoride-hexafluoropropylene (PVDF-co-EFP), polyvinylidenefluoride, polyacrylonitrile, polymethylmethacrylate, and so on.

The electrode of the lithium secondary battery according to the present invention may be manufactured using a conventional method. For example, electrode active material particles and a binder polymer are added to a solvent together with a conductive material and a dispersing agent as necessary to make slurry, and then the slurry is applied and compressed onto a current collector and then dried to make the electrode. At this time, it is obvious for any person having ordinary skill in the art to easily make a cathode while controlling thickness of the cathode active material layer applied on the current collector, amount of the binder polymer, process conditions or the like.

In addition, a separator is commonly interposed between the cathode and the anode, and the separator may use common porous polymer films used as conventional separators, such as porous polymer films made of ethylene homopolymer, propylene homopolymer, ethylene/butene copolymer, ethylene/hexene copolymer and ethylene/methacrylate copolymer, in single or in laminate. In other cases, the separator may use, but not limited to, common porous non-woven fabrics such as a non-woven fabric made of glass fiber with a high melt point or polyethylene terephthalate fiber.

The lithium secondary battery of the present invention may be, but not limited to, a cylindrical shape using a can, an angled shape, a pouch shape or a coin shape.

EXAMPLES

Hereinafter, the present invention is explained in more detail using examples. However, the following examples may be modified in various ways, and the present invention should not be interpreted as being limited thereto. The following examples are just given for persons having ordinary skill in the art to understand the present invention in a better way.

Example 1

1M of $LiPF_6$ was mixed to an organic solvent in which ethylene carbonate (EC), propylene carbonate (PC) and diethyl carbonate (DEC) were mixed at a ratio of 3:2:5 (w:w) to make a solution, and then 0.5 part by weight of vinyl ethylene carbonate (VEC) and 0.5 part by weight of butyronitrile (BN) were added to 100 parts by weight of the solution to make a nonaqueous electrolyte solution.

The above nonaqueous electrolyte solution was injected into a pouch battery having a cathode containing $LiCoO_2$ and $LiNi_{0.5}Mn_{0.3}Co_{0.2}O_2$ mixed at a weight ratio of 7:3 and an anode made of artificial graphite, thereby making a battery.

Initial efficiency, life cycle characteristics and thickness change at high-temperature swelling of the prepared pouch battery are recorded in the following table 1.

Example 2

A pouch battery was prepared in the same way as the example 1, except that the content of butyronitrile is changed into 2 parts by weight, based on 100 parts by weight of the nonaqueous electrolyte solution.

Example 3

A pouch battery was prepared in the same way as the example 1, except that the content of butyronitrile is changed into 5.0 parts by weight, based on 100 parts by weight of the nonaqueous electrolyte solution.

Example 4

A pouch battery was prepared in the same way as the example 1, except that the content of butyronitrile is changed into 10.0 parts by weight, based on 100 parts by weight of the nonaqueous electrolyte solution.

Example 5

A pouch battery was prepared in the same way as the example 1, except that the content of vinyl ethylene carbonate is changed into 1.0 parts by weight, based on 100 parts by weight of the nonaqueous electrolyte solution.

Example 6

A pouch battery was prepared in the same way as the example 5, except that the content of butyronitrile is changed into 2 parts by weight, based on 100 parts by weight of the nonaqueous electrolyte solution.

Example 7

A pouch battery was prepared in the same way as the example 5, except that the content of butyronitrile is changed into 5 parts by weight, based on 100 parts by weight of the nonaqueous electrolyte solution.

Example 8

A pouch battery was prepared in the same way as the example 5, except that the content of butyronitrile is changed into 10.0 parts by weight, based on 100 parts by weight of the nonaqueous electrolyte solution.

Example 9

A pouch battery was prepared in the same way as the example 1, except that the content of vinyl ethylene carbonate is changed into 3.0 parts by weight, based on 100 parts by weight of the nonaqueous electrolyte solution.

Example 10

A pouch battery was prepared in the same way as the example 9, except that the content of butyronitrile is changed into 2 parts by weight, based on 100 parts by weight of the nonaqueous electrolyte solution.

Example 11

A pouch battery was prepared in the same way as the example 9, except that the content of butyronitrile is changed into 5 parts by weight, based on 100 parts by weight of the nonaqueous electrolyte solution.

Example 12

A pouch battery was prepared in the same way as the example 9, except that the content of butyronitrile is changed into 10.0 parts by weight, based on 100 parts by weight of the nonaqueous electrolyte solution.

Example 13

A pouch battery was prepared in the same way as the example 1, except that the content of vinyl ethylene carbonate is changed into 5.0 parts by weight, based on 100 parts by weight of the nonaqueous electrolyte solution.

Example 14

A pouch battery was prepared in the same way as the example 13, except that the content of butyronitrile is changed into 2 parts by weight, based on 100 parts by weight of the nonaqueous electrolyte solution.

Example 15

A pouch battery was prepared in the same way as the example 13, except that the content of butyronitrile is changed into 5 parts by weight, based on 100 parts by weight of the nonaqueous electrolyte solution.

Example 16

A pouch battery was prepared in the same way as the example 13, except that the content of butyronitrile is changed into 10.0 parts by weight, based on 100 parts by weight of the nonaqueous electrolyte solution.

Example 17

A pouch battery was prepared in the same way as the example 9, except that 0.5 part by weight of valeronitrile was added instead of butyronitrile, based on 100 parts by weight of the nonaqueous electrolyte solution.

Example 18

A pouch battery was prepared in the same way as the example 9, except that 2 part by weight of valeronitrile was added instead of butyronitrile, based on 100 parts by weight of the nonaqueous electrolyte solution.

Example 19

A pouch battery was prepared in the same way as the example 9, except that 5 part by weight of valeronitrile was added instead of butyronitrile, based on 100 parts by weight of the nonaqueous electrolyte solution.

Example 20

A pouch battery was prepared in the same way as the example 9, except that 10.0 part by weight of valeronitrile was added instead of butyronitrile, based on 100 parts by weight of the nonaqueous electrolyte solution.

Example 21

A pouch battery was prepared in the same way as the example 17, except that an organic solvent in which ethylene carbonate (EC), propylene carbonate (PC) and ethyl propionate (EP) were mixed at a ratio of 3:2:5 (w:w) was used.

Example 22

A pouch battery was prepared in the same way as the example 18, except that an organic solvent in which ethylene carbonate (EC), propylene carbonate (PC) and ethyl propionate (EP) were mixed at a ratio of 3:2:5 (w:w) was used.

Example 23

A pouch battery was prepared in the same way as the example 19, except that an organic solvent in which ethylene carbonate (EC), propylene carbonate (PC) and ethyl propionate (EP) were mixed at a ratio of 3:2:5 (w:w) was used.

Example 24

A pouch battery was prepared in the same way as the example 20, except that an organic solvent in which ethylene carbonate (EC), propylene carbonate (PC) and ethyl propionate (EP) were mixed at a ratio of 3:2:5 (w:w) was used.

Example 25

A pouch battery was prepared in the same way as the example 6, except that only $LiNi_{0.5}Mn_{0.3}Co_{0.2}O_2$ was used as the cathode.

Example 26

A pouch battery was prepared in the same way as the example 6, except that only $LiNi_{0.8}Mn_{0.1}Co_{0.1}O_2$ was used as the cathode.

Example 27

A pouch battery was prepared in the same way as the example 6, except that the content and composition of the mixed organic solvent of the nonaqueous electrolyte solution was changed into ethylene carbonate (EC), ethyl methyl carbonate (EMC) and diethyl carbonate (DEC) mixed at a ratio of 3:4:3(w:w).

Comparative Example 1

A pouch battery was prepared in the same way as the example 1, except that vinyl ethylene carbonate (VEC) and butyronitrile (BN) were not added.

Comparative Example 2

A pouch battery was prepared in the same way as the comparative example 1, except that 3 parts by weight of vinylene carbonate (VC) was added, based on 100 parts by weight of the nonaqueous electrolyte solution.

Comparative Example 3

A pouch battery was prepared in the same way as the comparative example 1, except that 10.0 parts by weight of butyronitrile (BN) was added, based on 100 parts by weight of the nonaqueous electrolyte solution.

Comparative Example 4

A pouch battery was prepared in the same way as the comparative example 1, except that 10.0 parts by weight of valeronitrile (VN) was added, based on 100 parts by weight of the nonaqueous electrolyte solution.

Comparative Example 5

A pouch battery was prepared in the same way as the comparative example 1, except that 5.0 parts by weight of vinyl ethylene carbonate (VEC) was added, based on 100 parts by weight of the nonaqueous electrolyte solution.

Comparative Example 6

A pouch battery was prepared in the same way as the comparative example 1, except that 3.0 parts by weight of vinylene carbonate (VC) and 5.0 parts by weight of butyronitrile (BN) were added, based on 100 parts by weight of the nonaqueous electrolyte solution.

Comparative Example 7

A pouch battery was prepared in the same way as the comparative example 1, except that 3.0 parts by weight of vinylene carbonate (VC) and 5.0 parts by weight of valeronitrile (VN) were added, based on 100 parts by weight of the nonaqueous electrolyte solution.

Comparative Example 8

A pouch battery was prepared in the same way as the comparative example 1, except that only $LiNi_{0.5}Mn_{0.3}Co_{0.2}O_2$ was used as the cathode.

Comparative Example 9

A pouch battery was prepared in the same way as the comparative example 1, except that only $LiNi_{0.8}Mn_{0.1}Co_{0.1}O_2$ was used as the cathode.

Comparative Example 10

A pouch battery was prepared in the same way as the comparative example 1, except that only $LiCoO_2$ was used as the cathode.

Comparative Example 11

A pouch battery was prepared in the same way as the comparative example 8, except that 3.0 parts by weight of vinyl ethylene carbonate (VEC) and 2.0 parts by weight of acetonitrile (AcN) were added to 100 parts by weight of the nonaqueous electrolyte solution.

Evaluation of Initial Performance and Life Performance of Battery

After an electrolyte solution was injected into the pouch batteries prepared in accordance with the examples and the comparative examples, the pouch batteries were aged for 2 days and then charged at 0.2 C rate for 50 minutes. Subsequently, the batteries were degassed and resealed and then charged at 0.2 C at a room temperature under a constant current/constant voltage condition, and then discharged at 0.2 C to 3.0V under a constant current condition, which is called an initial charging/discharging. At this time, a ratio of a charge capacity to a discharge capacity is called initial efficiency. After the initial charging/discharging, the batteries were charged/discharged 400 times at 1.0 C-rate in the same voltage region. A capacity retention ratio at 400th charging/discharging in comparison to the initial discharge capacity is shown in the following table 1.

Evaluation of Change of Thickness at High-Temperature Storage

After the pouch batteries prepared in accordance with the examples and the comparative examples were initially charged/discharged in the above way, the pouch batteries were charged/discharged at 1.0 C-rate 4 times in the same voltage region, charged at 1.0 C-rate to 4.2V, then heated from a normal temperature to 90° C. for 1 hour, and then maintained at 90° C. for 4 hours. After that, the change of thicknesses from a normal temperature to a high temperature was measured. An increase rate of thickness is listed in the following table 1.

TABLE 1

| | Initial Efficiency (%) | Capacity Retention Rate at $400^{th}$ (%) | Thickness Change at High temperature (mm) |
|---|---|---|---|
| Example 1 | 90.1 | 80.6 | 1.98 |
| Example 2 | 90.2 | 79.8 | 1.68 |
| Example 3 | 90.1 | 76.9 | 0.90 |
| Example 4 | 90.2 | 73.7 | 0.70 |
| Example 5 | 90.0 | 83.4 | 1.79 |
| Example 6 | 90.0 | 83.0 | 1.42 |
| Example 7 | 90.2 | 82.1 | 0.72 |
| Example 8 | 90.4 | 78.7 | 0.57 |
| Example 9 | 90.4 | 86.3 | 1.03 |
| Example 10 | 90.5 | 86.2 | 0.90 |
| Example 11 | 90.4 | 85.3 | 0.55 |
| Example 12 | 90.1 | 84.3 | 0.40 |
| Example 13 | 90.0 | 86.9 | 0.87 |
| Example 14 | 90.4 | 86.9 | 0.70 |
| Example 15 | 90.1 | 86.7 | 0.48 |
| Example 16 | 90.4 | 86.3 | 0.28 |
| Example 17 | 90.4 | 86.2 | 1.06 |
| Example 18 | 90.4 | 86.0 | 0.90 |
| Example 19 | 90.2 | 85.2 | 0.61 |
| Example 20 | 90.0 | 84.5 | 0.41 |
| Example 21 | 90.5 | 86.6 | 1.24 |
| Example 22 | 90.6 | 86.3 | 1.09 |
| Example 23 | 90.6 | 86.5 | 0.68 |
| Example 24 | 90.7 | 85.3 | 0.46 |
| Example 25 | 88.9 | 84.2 | 1.79 |
| Example 26 | 87.5 | 82.6 | 2.04 |
| Example 27 | 90.6 | 82.8 | 1.56 |
| Comparative Example 1 | 81.7 | 6.4 | 2.65 |
| Comparative Example 2 | 90.7 | 87.6 | 2.98 |
| Comparative Example 3 | 66.6 | 5.2 | 2.31 |
| Comparative Example 4 | 67.4 | 7.3 | 2.37 |
| Comparative Example 5 | 90.2 | 87.0 | 2.13 |
| Comparative Example 6 | 90.1 | 85.0 | 2.46 |
| Comparative Example 7 | 90.0 | 85.7 | 2.54 |
| Comparative Example 8 | 82.3 | 5.5 | 3.35 |
| Comparative Example 9 | 81.2 | 6.9 | 3.95 |
| Comparative Example 10 | 81.2 | 19.1 | 0.32 |
| Comparative Example 11 | 65.7 | 0.2 | 2.94 |

What is claimed is:

1. A lithium secondary battery comprising an anode capable of intercalating or disintercalating lithium ions, a cathode configured with a lithium-containing oxide, and a nonaqueous electrolyte solution, wherein the lithium-containing oxide comprises a lithium nickel based oxide, and the nonaqueous electrolyte solution comprises vinyl ethylene carbonate (VEC) of the following chemistry figure 1 and a mono-nitrile compound of the following chemistry figure 2 at the same time:

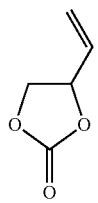

<Chemistry Figure 1>

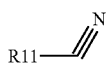

<Chemistry Figure 2> wherein R11 is an alkyl group having 3 to 4 carbons,
wherein the amount of the vinyl ethylene carbonate is 3.0 parts by weight based on 100 parts by weight of the nonaqueous electrolyte solution, and the amount of the mono-nitrile compound is 2.0 parts by weight based on 100 parts by weight of the nonaqueous electrolyte solution.

2. The lithium secondary battery according to claim 1, wherein the lithium nickel based oxide is any one selected from the group consisting of $LiNiO_2$; $Li_{1-x}(Ni_aCo_bMn_c)O_2$, wherein $-0.1 \leq x \leq 0.1$, $0<a<1$, $0<b<1$, $0<c<1$, and $a+b+c=1$; $LiNi_{1-y}Co_yO_2$, wherein $0 \leq y<1$; $LiNi_{1-y}Mn_yO_2$, wherein $0 \leq y<1$; $Li(Ni_aCo_bMn_c)O_4$, wherein $0<a<2$, $0<b<2$, $0<c<2$, and $a+b+c=2$; $LiMn_{2-z}Ni_zO_4$, wherein $0<z<2$, and mixtures thereof.

3. The lithium secondary battery according to claim 1, wherein the lithium nickel based oxide is $Li_{1-x}(Ni_aCo_bMn_c)O_2$, wherein $-0.1 \leq x \leq 0.1$, $0<a<1$, $0<b<1$, $0<c<1$, and $a+b+c=1$.

4. The lithium secondary battery according to claim 1, wherein the lithium nickel based oxide is $Li_{1-x}(Ni_aCo_bMn_c)O_2$, wherein $-0.1 \leq x \leq 0.1$, $0.5 \leq a \leq 0.8$, $0.1 \leq b \leq 0.2$, $0.1 \leq c \leq 0.3$, and $a+b+c=1$.

5. The lithium secondary battery according to claim 1, wherein the lithium-containing oxide is a mixture of the lithium nickel based oxide and $LiCoO_2$.

6. The lithium secondary battery according to claim 5, wherein the lithium nickel based oxide is any one selected from the group consisting of $LiNiO_2$; $Li_{1-x}(Ni_aCo_bMn_c)O_2$, wherein $-0.1 \leq x \leq 0.1$, $0<a<1$, $0<b<1$, $0<c<1$, and $a+b+c=1$; $LiNi_{1-y}Co_yO_2$, wherein $0 \leq y<1$; $LiNi_{1-y}Mn_yO_2$, wherein $0 \leq y<1$; $Li(Ni_aCo_bMn_c)O_4$, wherein $0<a<2$, $0<b<2$, $0<c<2$, and $a+b+c=2$; $LiMn_{2-z}Ni_zO_4$, wherein $0<z<2$, and mixtures thereof.

7. The lithium secondary battery according to claim 5, wherein the lithium nickel based oxide is $Li_{1-x}(Ni_aCo_bMn_c)O_2$, wherein $-0.1 \leq x \leq 0.1$, $0<a<1$, $0<b<1$, $0<c<1$, and $a+b+c=1$.

8. The lithium secondary battery according to claim 5, wherein the lithium nickel based oxide is $Li_{1-x}(Ni_aCo_bMn_c)O_2$, wherein $-0.1 \leq x \leq 0.1$, $0.5a0.8$, $0.1 \leq b \leq 0.2$, $0.1 \leq c \leq 0.3$, and $a+b+c=1$.

9. The lithium secondary battery according to claim 1, wherein the mono-nitrile compound is any one selected from the group consisting of butyronitrile, valeronitrile, and mixtures thereof.

10. The lithium secondary battery according to claim 1, wherein the nonaqueous electrolyte solution comprises a mixed organic solvent comprising a cyclic carbonate compound of the following chemistry figure 3 and a linear carbonate compound of the following chemistry figure 4:

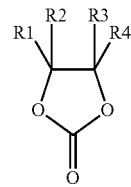

<Chemistry Figure 3> wherein R1 to R4 are independently selected from the group consisting of hydrogen atoms, fluorine and alkyl groups having 1 to 4 carbons, and

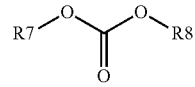

<Chemistry Figure 4> wherein R7 and R8 are independently alkyl groups having 1 to 4 carbons, wherein at least one hydrogen atom of the alkyl group is replaceable with fluorine.

11. The lithium secondary battery according to claim 10, wherein the cyclic carbonate compound is ethylene carbonate or a mixture of ethylene carbonate and propylene carbonate.

12. The lithium secondary battery according to claim 10, wherein the mixed organic solvent further comprises a linear ester compound of the following chemistry figure 5:

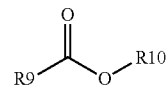

<Chemistry Figure 5> wherein R9 and R10 are independently alkyl groups having 1 to 4 carbons, wherein at least one hydrogen atom of the alkyl group is replaceable with fluorine.

13. The lithium secondary battery according to claim 12, wherein the linear ester compound is ethyl propionate.

14. The lithium secondary battery according to claim 1, wherein the nonaqueous electrolyte solution comprises a mixed organic solvent comprising a cyclic carbonate compound of the following chemistry figure 3 and a linear ester compound of the following chemistry figure 5:

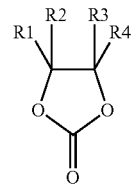

<Chemistry Figure 3> wherein R1 to R4 are independently selected from the group consisting of hydrogen atoms, fluorine and alkyl groups having 1 to 4 carbons, and <Chemistry Figure 5>

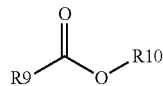

wherein R9 and R10 are independently alkyl groups having 1 to 4 carbons, wherein at least one hydrogen atom of the alkyl group is replaceable with fluorine.

15. The lithium secondary battery according to claim 13, wherein the linear ester compound is ethyl propionate.

16. The lithium secondary battery according to claim 1, wherein the lithium secondary battery has an initial efficiency ranging from 87.5 percent to 90.7 percent, wherein the initial efficiency is a ratio of a charge capacity to a discharge capacity of the battery, wherein the charge capacity was determined by charging the battery at 0.2 C rate at a constant voltage and a constant current, and wherein the discharge capacity was determined by discharging the battery at 0.2 C rate to 3.0 Volts (V) under the constant current.

17. The lithium secondary battery according to claim 16, wherein the lithium secondary battery has capacity retention rate at a 400$^{th}$ charging/discharging ranging from 73.7 percent to 86.9 percent, wherein the capacity retention rate is a ratio of a charge capacity to a discharge capacity at the 400$^{th}$ charging/discharging of the battery, wherein the charge capacity was determined by charging the battery at 1.0 C rate at the constant voltage and the constant current, and wherein the discharge capacity was determined by discharging the battery at 1.0 C rate to 3.0 Volts (V) under the constant current.

18. The lithium secondary battery according to claim 17, wherein the lithium secondary battery has a thickness change at 90 degrees Celsius ranging from 0.28 millimeters (mm) to 2.04 mm, wherein the thickness change was determined by the following steps:
 (1) charging at 1.0 C rate at the constant current and the constant voltage;
 (2) discharging at 1.0 C rate to about 3.0 V under the constant current;
 (3) repeating steps (1) and (2) four times;
 (4) charging at 1.0 C rate to about 4.2 V;
 (5) heating from a normal temperature to 90 degrees Celsius for 1 hour;
 (6) maintaining the temperature of the battery at 90 degrees Celsius for 4 hours; and
 (7) measuring the change in thickness from the normal temperature to 90 degrees Celsius.

* * * * *

UNITED STATES PATENT AND TRADEMARK OFFICE
CERTIFICATE OF CORRECTION

PATENT NO. : 8,808,927 B2
APPLICATION NO. : 12/740491
DATED : August 19, 2014
INVENTOR(S) : Jong-Ho Jeon, Soo-Jin Kim and Ho-Chun Lee It is certified that error appears in the above-identified patent and that said Letters Patent is hereby corrected as shown below:

In the claims
Column 13, line 47, "$LiMn_{2-z}Ni_3O_4$" should read -- $LiMn_{2-z}Ni_zO_4$ --.
Column 13, line 56, "0.5a0.8" should read -- $0.5 \leq a \leq 0.8$ --.

Signed and Sealed this
Sixteenth Day of February, 2016

Michelle K. Lee
*Director of the United States Patent and Trademark Office*